United States Patent
Kawamura

(10) Patent No.: US 9,561,329 B2
(45) Date of Patent: Feb. 7, 2017

(54) PISTON FOR SYRINGE HAVING VERY SMALL CAPACITY, AND PLUNGER HAVING THE PISTON MOUNTED THERETO

(75) Inventor: Hideaki Kawamura, Tokyo (JP)

(73) Assignee: DAIKYO SEIKO, LTD., Tokyo (JP)

(*) Notice: Subject to any disclaimer, the term of this patent is extended or adjusted under 35 U.S.C. 154(b) by 53 days.

(21) Appl. No.: 13/381,320

(22) PCT Filed: Jun. 22, 2010

(86) PCT No.: PCT/JP2010/060508
§ 371 (c)(1),
(2), (4) Date: Dec. 28, 2011

(87) PCT Pub. No.: WO2011/007644
PCT Pub. Date: Jan. 20, 2011

(65) Prior Publication Data
US 2012/0109076 A1    May 3, 2012

(30) Foreign Application Priority Data

Jul. 17, 2009  (JP) .................................. 2009-169261

(51) Int. Cl.
*A61M 5/31*    (2006.01)
*A61M 5/315*    (2006.01)

(52) U.S. Cl.
CPC ...... *A61M 5/31515* (2013.01); *A61M 5/31513* (2013.01)

(58) Field of Classification Search
CPC ..................... A61M 5/31511; A61M 5/31515; A61M 5/1452

(Continued)

(56) References Cited

U.S. PATENT DOCUMENTS 2,490,553 A * 12/1949 Smith .............................. 604/89
3,058,467 A * 10/1962 Faure ............................. 206/221

(Continued)

FOREIGN PATENT DOCUMENTS

JP    06-343677    12/1994
JP    2000-140103    5/2000

(Continued)

*Primary Examiner* — Scott Medway
(74) *Attorney, Agent, or Firm* — Hamre, Schumann, Mueller & Larson, P.C.

(57) ABSTRACT

Disclosed are a piston for a micro-volume syringe and a plunger. The micro-volume syringe has a syringe barrel with a space defined in it. The piston is slidable on and along a wall of the space. A leading member to be arranged on a side where the piston comes into contact with a solution filled in the space and a trailing member to be arranged on a side where a plunger rod is to be connected, the latter side being opposite to a solution side of the leading member, have been integrated with each other. The trailing member has a higher hardness than the leading member. With the micro-volume syringe in which a drug solution can be filled in a very small quantity, the piston makes it possible to perform smooth drawing and ejection of the drug solution without leakage. Even if the small piston connected to a tip of the plunger rod is operated in a direction that the piston is to be pulled out of the syringe, the plunger rod does not slip off from the piston accidentally. The piston and plunger are optimal for the micro-volume syringe.

9 Claims, 7 Drawing Sheets

(58) Field of Classification Search
USPC .......................................... 604/131, 121, 218
See application file for complete search history.

(56) References Cited

U.S. PATENT DOCUMENTS

| | | | | |
|---|---|---|---|---|
| 3,164,303 | A * | 1/1965 | Trautmann ..................... | 222/190 |
| 3,747,479 | A * | 7/1973 | Nightingale et al. ........... | 92/203 |
| 3,811,441 | A * | 5/1974 | Sarnoff ........................ | 604/201 |
| 3,902,491 | A * | 9/1975 | Lajus ............................ | 604/221 |
| 4,507,117 | A * | 3/1985 | Vining et al. ................. | 604/196 |
| 4,677,980 | A * | 7/1987 | Reilly et al. .................. | 600/432 |
| 4,710,170 | A * | 12/1987 | Haber et al. ................... | 604/110 |
| 4,911,695 | A * | 3/1990 | Lindner ........................ | 604/228 |
| 4,997,423 | A * | 3/1991 | Okuda et al. .................. | 604/230 |
| 5,004,460 | A * | 4/1991 | Gimeno ........................ | 604/228 |
| 5,007,904 | A * | 4/1991 | Densmore et al. ........... | 604/228 |
| 5,300,031 | A * | 4/1994 | Neer et al. ..................... | 604/154 |
| 5,314,415 | A * | 5/1994 | Liebert et al. ................ | 604/218 |
| 5,383,858 | A * | 1/1995 | Reilly et al. .................. | 604/152 |
| 5,411,488 | A * | 5/1995 | Pagay et al. .................. | 604/218 |
| 5,489,266 | A * | 2/1996 | Grimard ........................ | 604/89 |
| 5,535,746 | A * | 7/1996 | Hoover et al. ................ | 600/432 |
| 5,605,542 | A * | 2/1997 | Tanaka et al. ................. | 604/89 |
| 5,776,138 | A * | 7/1998 | Vidal et al. ................... | 606/107 |
| 5,865,803 | A * | 2/1999 | Major ........................... | 604/122 |
| 5,980,487 | A * | 11/1999 | Jones et al. ................... | 604/110 |
| 6,004,300 | A * | 12/1999 | Butcher et al. ............... | 604/222 |
| 6,017,330 | A * | 1/2000 | Hitchins et al. .............. | 604/218 |
| 6,196,999 | B1 * | 3/2001 | Goethel et al. ............... | 604/131 |
| 6,659,754 | B1 * | 12/2003 | Smith .................... | 425/174.8 E |
| 7,101,354 | B2 * | 9/2006 | Thorne et al. ................ | 604/191 |
| 7,547,297 | B2 * | 6/2009 | Brinkhues ..................... | 604/199 |
| 7,727,202 | B2 * | 6/2010 | Kirchhofer ....... | A61M 5/31513 |
| | | | | 604/187 |
| 7,749,202 | B2 * | 7/2010 | Miller et al. .................. | 604/222 |
| 7,766,882 | B2 * | 8/2010 | Sudo et al. .................... | 604/218 |
| 8,137,307 | B2 * | 3/2012 | Tennican et al. .............. | 604/89 |
| 9,101,720 | B2 * | 8/2015 | Okihara et al. | |
| 2007/0060896 | A1 | 3/2007 | Miller et al. | |
| 2007/0265574 | A1* | 11/2007 | Tennican et al. ............. | 604/190 |
| 2008/0041885 | A1* | 2/2008 | Costa et al. ................... | 222/386 |
| 2010/0106086 | A1 | 4/2010 | Sudo et al. | |

FOREIGN PATENT DOCUMENTS

| | | |
|---|---|---|
| JP | 2007-289676 | 11/2007 |
| JP | 2009-505794 | 2/2009 |
| WO | WO 2006/087762 | 8/2006 |
| WO | WO 2008/156216 | 12/2008 |

* cited by examiner

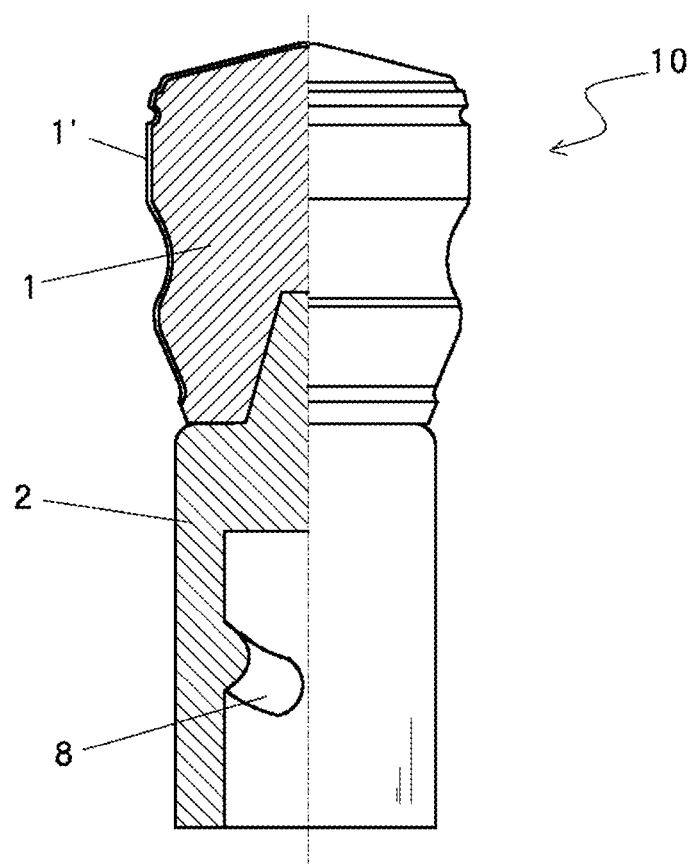

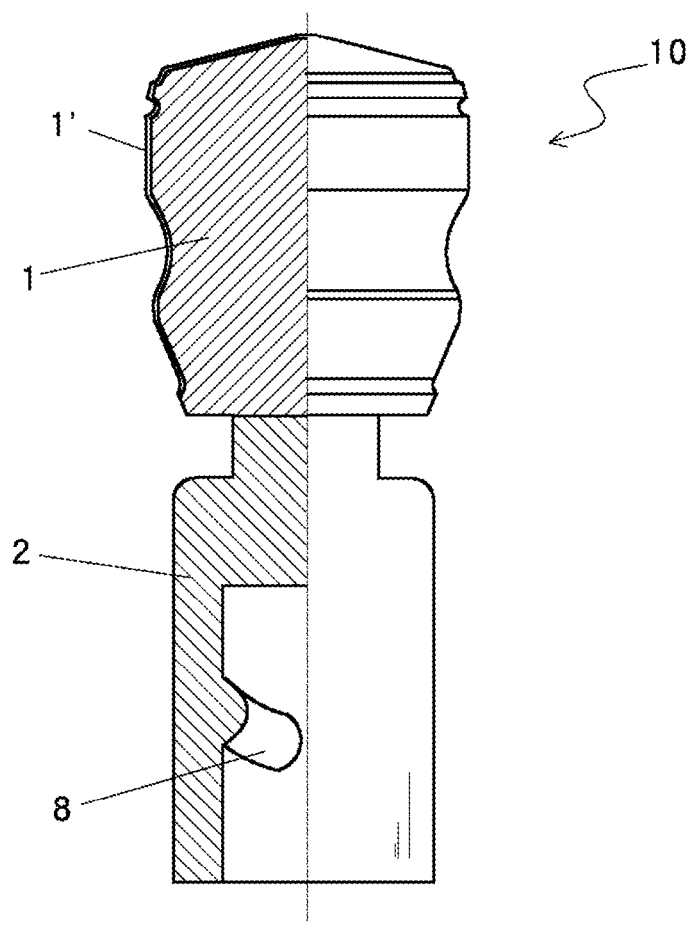

PISTON FOR SYRINGE HAVING VERY SMALL CAPACITY, AND PLUNGER HAVING THE PISTON MOUNTED THERETO

TECHNICAL FIELD

The present invention relates to a piston for a syringe with an extremely small fill capacity for a drug solution (hereinafter called "micro-volume syringe") and also to a plunger having the piston connected thereto. More specifically, the present invention is concerned with a piston for a micro-volume syringe—which, when connected to a plunger rod, is firmly fixed, remains stably in the fixed state, does not slip off accidentally from the plunger rod, and further, is allowed to slide as desired on and along a wall of a narrow space in a syringe barrel, in which a drug solution is filled, without accidentally slipping off from the plunger rod—and also with a plunger having the piston connected thereto.

BACKGROUND ART

In recent years, the elucidation of disease causes is proceeding on a gene level, and the advances in medical treatment have made brilliant achievements. Keeping in step with these changes, the developments of prescription products vary widely so that a need has arisen to inject an extremely small quantity of a drug solution into the body by a syringe. In such a situation, a micro-volume syringe that the quantity of a drug solution to be filled in a syringe barrel is, for example, as little as 1 mL or smaller or even 0.25 mL is used. As in the before, such a micro-volume syringe is also comprised basically of a syringe barrel, a piston slidable in the syringe barrel, and a plunger rod for pushing the piston.

In general, a piston and a plunger rod, which serves to cause the piston to slide, are connected to each other by keeping a threaded portion, which is arranged at a tip of the plunger rod, in engagement with a threaded portion in a cavity which the piston is provided with (see, for example, Patent Document 1). In view of its clinical application, the piston is required to have performance to be described hereinafter. Firstly, contamination of a drug solution from the material forming the piston needs to be avoided, and therefore, the material forming especially a forward end portion that comes into contact with the drug solution is required to have excellent chemical resistance. Further, the piston connected to the tip of the plunger rod is required to be smoothly slidable on and along a wall of a syringe barrel without causing leakage upon filling the drug solution into the syringe barrel or ejecting it from the syringe barrel. As the performance of the piston, smooth slidability is hence required in addition to sealing performance.

Concerning the piston-forming material required to have the above-described performance, it has been proposed to cover a surface of a piston, which is formed of a synthetic rubber, with a fluorinated resin (see Patent Document 2). However, a plunger rod arranged in threaded engagement with a piston may accidentally slip off from the piston when the plunger rod is handled to pull out the piston from the syringe barrel. This problem pronouncedly arises when a piston formed of such a covered synthetic rubber is used. Proposals have also been made to avoid such a problem (see, for example, Patent Document 3). It is to be noted that the manner of connection between the piston and plunger rod is not limited to their threaded engagement but includes fitting an anchor-shaped portion, which is arranged on the tip of the plunger rod, in a cavity arranged in the piston (see, for example, Patent Document 4).

PRIOR ART DOCUMENTS

Patent Documents

Patent Document 1: JP-A-2007-289676
Patent Document 2: JP-A-06-343677
Patent Document 3: JP-A-2000-140103
Patent Document 4: WO-A-2006-087762

DISCLOSURE OF THE INVENTION

Problem to Be Solved by the Invention

Similar to syringes of regular size, micro-volume syringes the developments of which have been under way in recent years also involve the problem that a piston connected to the tip of a plunger rod may slip off accidentally from the plunger rod. According to a study by the present inventors, a micro-volume syringe is comprised of a combination of an extremely slender plunger rod and an extremely small piston from the standpoint of the ease of handling. Their threadedly engaged portions or fitted portions are hence very small, and compared with the syringes of regular size, the piston connected to the tip of the plunger rod has a high tendency to accidentally slip off from the plunger rod. Especially when a piston of extremely small size connected to the tip of a slender plunger rod is moved in a direction that the piston is to be pulled out of a cylinder barrel, the plunger rod has a profoundly high tendency to accidentally slip off from the piston, thereby imposing a limitation on the manner of use. With the foregoing in view, the present inventors have come to recognize that the above-described tendency is a problem to be solved with respect to micro-volume syringes. Described specifically, with a conventional plunger rod and piston applied to a micro-volume syringe barrel, it is difficult to draw a drug solution into the syringe barrel by moving the piston connected to the tip of the plunger rod in the direction that the piston is to be pulled out although the drug solution may be ejected by pushing the piston. Quite obviously, the manner of use practiced with the syringes of conventional size, including a drawing operation, is considered to be practically impossible.

Therefore, objects of the present invention are to provide a piston optimal for a syringe with an extremely small fill capacity for a drug solution, i.e., a micro-volume syringe that, even when the piston especially in the form of a small piston connected to a tip of a slender plunger rod is operated by the plunger rod in a direction that the piston is to be pulled out of a syringe barrel, the plunger rod does not accidentally slip off from the piston, and a plunger having the piston connected thereto. Further objects of the present invention are to provide a piston for a micro-volume syringe that a sealed leakage-free space can be formed by the piston connected to a tip of a plunger rod and the piston is allowed to smoothly and repeatedly slide on and along a wall of an extremely narrow space in the syringe barrel, and a plunger having the piston connected thereto.

Means for Solving the Problem

The above-described objects can be achieved by the present invention to be described hereinafter. Described specifically, the present invention provides a piston for a micro-volume syringe having a syringe barrel with a space defined therein, said piston being slidable on and along a wall of the space, characterized in that a leading member to be arranged on a side where the piston comes into contact with a solution filled in the space and a trailing member to be arranged on a side where a plunger rod is to be connected, the latter side being opposite to a solution side of the leading member, have been integrated with each other, and the trailing member has a higher hardness than the leading member.

The present invention also include the following preferred embodiments: the piston as described above, wherein a bottom wall portion of the leading member and a forward end portion of the trailing member, said forward end portion having a flat wall, have been integrated with each other by welding, and the flat wall of the trailing member before the integration has a smaller outer diameter than the bottom wall portion of the leading member before the integration; the piston as described above, wherein the leading member before the integration is provided with a recess through a bottom wall portion thereof on a side opposite to a side where the leading member comes into contact with the solution, the trailing member before the integration is provided on a side of the leading member thereof with a cylindrical or truncated conical protrusion and is provided on a side thereof opposite to the side of the forward end portion with a bore for the connection of the plunger rod, and the leading member and trailing member have been integrated with each other by welding with the protrusion of the trailing member being fitted in the recess of the leading member; the piston as described above, wherein the leading member is formed of a material, which is composed as a primary component of a material selected from the group consisting of synthetic rubbers and thermoplastic elastomers and which has a hardness of from 40 to 70; the piston as described above, wherein the trailing member is formed of a material, which is selected from the group consisting of polyethylene, polypropylene, polycarbonates and thermoplastic elastomers and which has a hardness of 75 or higher; and the piston as described above, wherein the leading member is covered, over at least a surface thereof where the leading member comes into contact with the solution, with a resin selected from the group consisting of fluorinated resins, polyethylene resin, polypropylene resin and ultra high molecular polyethylene resin.

The present invention also provides a piston-connected plunger characterized in that a plunger rod is threadedly connected at a tip thereof to a ridge arranged on an inner wall of a bore formed in the trailing member of any one of the above-described pistons.

Advantageous Effects of the Invention

According to the present invention, there are provided a piston optimal for a syringe with an extremely small fill capacity for a drug solution, i.e., a micro-volume syringe that, even when the piston especially in the form of a small piston connected to a tip of a slender plunger rod is operated by the plunger rod in a direction that the piston is to be pulled out of a syringe barrel, the plunger rod does not accidentally slip off from the piston, and a plunger having the piston connected thereto. According to the present invention, there are also provided a piston for a micro-volume syringe that a sealed, leakage-free, good space can be formed by the piston connected to a tip of a plunger rod and the piston can be caused to smoothly and repeatedly slide on and along a wall that defines an extremely narrow space in the syringe barrel, and a plunger having the piston connected thereto.

BRIEF DESCRIPTION OF THE DRAWINGS

FIG. 5(a) is a schematic cross-sectional view for describing one example of the construction of the piston according to the present invention.

FIG. 5(b) is a schematic cross-sectional view for describing another example of the construction of the piston according to the present invention.

MODES FOR CARRYING OUT THE INVENTION

The present invention will hereinafter be described in further detail based on preferred embodiments. As a result of an enthusiastic investigation by the present inventors to solve the above-described problems of the conventional technologies, it has been found that despite the extremely small size of a piston to permit its application to a micro-volume syringe barrel, the designing of the piston in a particular shape and structure permits smooth sliding of the piston in a narrow space of a syringe barrel, to say nothing of excellent sealing performance and the occurrence of no leakage, leading to the present invention. More specifically, it has been found that a piston equipped with the above-described excellent functions can be obtained by forming the piston with two members, one being a leading member as a section that comes into contact with a drug solution, and the other a trailing member as another section to which a plunger rod is connected, and integrating them together and also by designing the leading member and trailing member such that the latter has a higher hardness than the former.

Figure 6A:
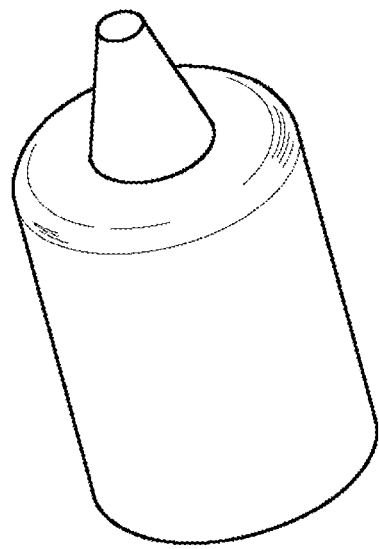
FIG. 6(a) is a schematic cross-sectional view of another illustrative shape of the trailing member constituting the another section of the piston according to the present invention.
Figure 6B:
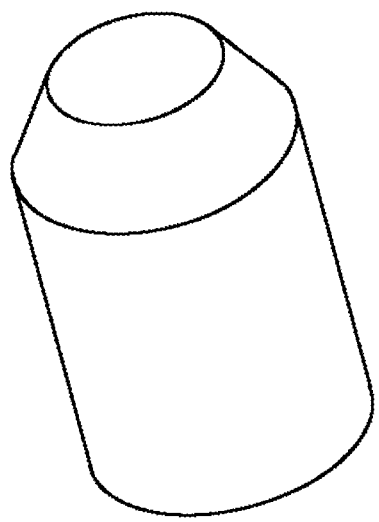
FIG. 6(b) is a schematic cross-sectional view of a further illustrative shape of the trailing member constituting the another section of the piston according to the present invention.
Figure 6C:
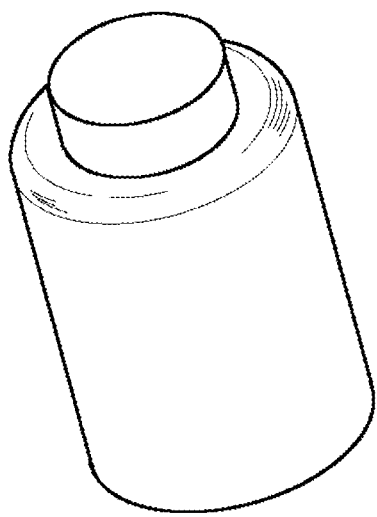
FIG. 6(c) is a schematic cross-sectional view of a still further illustrative shape of the trailing member constituting the another section of the piston according to the present invention.

More preferably, the shape and structure of the trailing member, which is to be integrated with the leading member, are designed such that a slender plunger rod can be firmly connected to the trailing member, and the trailing member having the above-described shape and structure is welded with the leading member to integrate them together. Although no particular limitation is imposed on the manner of welding upon integration, the leading member and trailing member can be easily and firmly integrated together, for example, in a manner to be described below. The leading member and trailing member may be brought into a more firmly connected state, for example, by arranging, for example, such a cylindrical or truncated conical protrusion as depicted in FIG. 6(a), 6(b) or 6(c) on the side of a forward end of the trailing member of the piston, fitting the protrusion in a recess arranged in the leading member of the piston on a side opposite to a solution side of the leading member, and welding the leading member and trailing member in the fitted state to integrate them together (see FIG. 1, FIG. 5(a) or FIG. 5(b)). Of course, the joint surfaces of both the members may be flat without forming them in such fitting structures. However, the arrangement of such fitting structures as described above can bring about advantageous effects to be described below. Firstly, the arrangement of the fitting structures can effectively avoid an axial misalignment between both the members. Further, the arrangement of the fitting structures can increase the area of contact so that the strength of connection can be enhanced. Furthermore, effects of physical connection can be also expected. It is to be noted that the leading member and trailing member can be integrated together by applying an adhesive therebetween. It is, however, impossible to deny the potential risk that one or more components contained in the adhesive may affect a drug solution to be filled in the syringe. It is, therefore, more preferred to integrate them with each other by relying upon welding of their materials themselves without using such an adhesive. As materials for forming the leading member and trailing member, the use of those weldable with each other is preferred accordingly.

Upon welding the leading member and trailing member to integrate them together, various welding methods can be used. Examples include: to insert a forward end portion of a leading member, which has been molded beforehand, in a mold and then to injection-mold a trailing member to integrate them together; to thermally fuse both a rearward end portion of a leading member and a forward end portion of the trailing member and to bring them into contact with each other; and to apply ultrasonic vibrations to the leading member and trailing member while keeping them in contact with each other, thereby welding them together. The materials of portions to be brought into contact with each other may preferably be similar materials so that sufficient strength can be provided upon welding. Depending on circumstances, it may also be effective to insert, as a joining member, a material having high weldability with both the members. About suitable materials, a description will be made subsequently herein.

To the piston according to the present invention which has such a shape and structure as described above, a plunger rod is connected, for example, by threadedly fitting the plunger rod at a tip thereof in a bore arranged in the trailing member of the piston on a side opposite to the welded leading member, and the piston is used in this state. As the piston is firmly connected to the plunger rod, the plunger in this state can be used in a similar manner as a plunger in a syringe of regular size.

Figure 1:
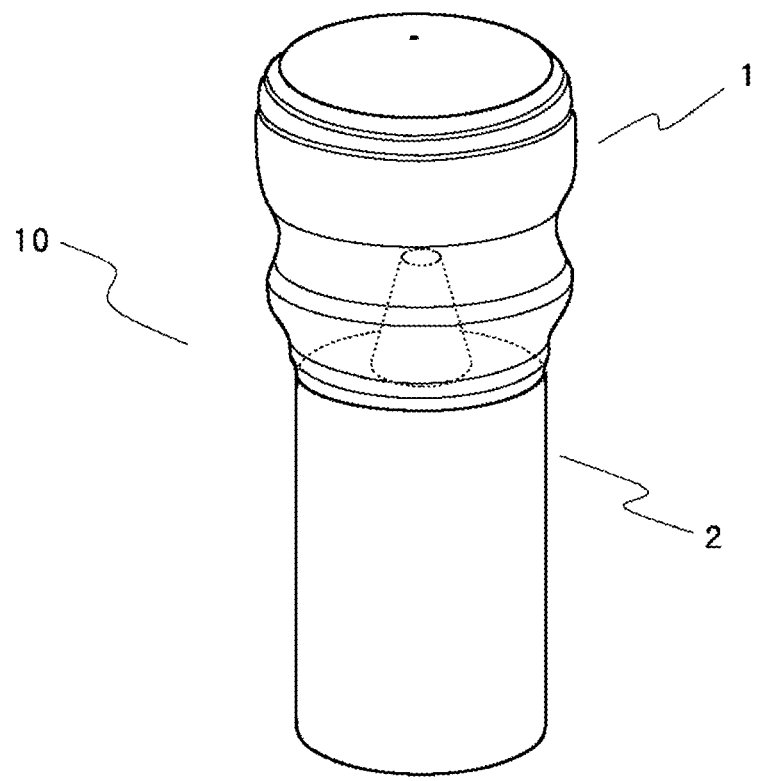
FIG. 1 is a schematic perspective view showing one embodiment of the piston according to the present invention.

With reference to the drawings, a more detailed description will be made about the piston according to the present invention for the micro-volume syringe and the plunger having the piston connected thereto. As shown in FIG. 1, the piston according to the present invention is comprised of two members, one being a leading member 1 which comes into contact with a drug solution and is equipped the primary function of the piston, and the other a trailing member 2 adapted to firmly connect a plunger rod. Preferably, they may be formed of materials which can exhibit their respective functions at a high level, respectively. It is, however, more preferred to form the weld portions of these leading member 1 and trailing member 2 with mutually-compatible materials or similar materials, respectively, because they need to be integrated by welding.

Figure 2:
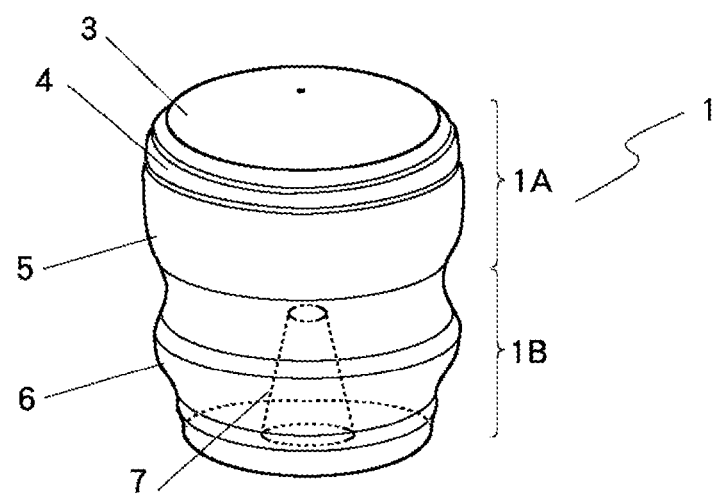
FIG. 2 is a perspective view of a leading member constituting a section of the piston of FIG. 1.

As the material for forming the leading member 1 that constitutes one of the sections of the piston according to the present invention as shown in FIG. 2, various synthetic rubbers having excellent elasticity and thermoplastic elastomers having excellent weldability with plastic materials, like usual piston materials, can be used as desired. Depending on circumstances, it may also be preferred to use them in combination such that the leading member 1 is formed with a synthetic rubber and only its joint portion with the trailing member 2 is formed with a thermoplastic elastomer. Synthetic rubbers, which are excellent in elasticity and are usable in the present invention, include, for example, butyl rubber (IIR), chlorinated butyl rubber (CIIR), brominated butyl rubber (BIIR), partially-crosslinked IIR, polybutadienes rubber (BR), polyisoprenes rubber (IR), ethylene-propylene-diene terpolymer rubbers (EPDM), styrene-butadiene copolymer rubber (SBR), acrylic rubbers (ACM), acrylonitrile-butadiene rubber (NMR), and the like.

Examples of the thermoplastic elastomer useful in the present invention include polyisobutylene-based thermoplastic elastomers (SIBS); styrene-based elastomers such as styrene-butadiene-styrene (SBS)-based copolymers, styrene-ethylene/butylene-styrene (SEBS)-based copolymers and styrene-isoprene-styrene (SIS)-based copolymers; and olefin-based elastomers such as ethylene-propylene-noncojugated diene monomer (EPDM)-based copolymers and ethylene-propylene (EPM)-based copolymers. Particularly preferred are butyl-based rubbers (IIR, CIIR, BIIR) excellent in rubber elasticity and dissolution characteristics; and those obtained by copolymerizing polyethylene or polybutylene as soft segments in the form of blocks in polystyrene as hard segments such that the resulting SEBS elastomers are partially or completely crosslinked. Completely crosslinked, thermoplastic elastomers are especially suited as materials for forming the piston according to the present invention, because they are very close in physical properties to rubbers and are excellent in sealing performance, chemical resistance, processability, the dimensional accuracy of products, and the possibility of thermal welding with other resins.

The leading member formed of such a material as described above may have preferably a hardness of from 40 to 70, more preferably a hardness of from 50 to 60 in terms of the Shore A hardness from the standpoint of the designing convenience of the member. No particular limitation is, however, imposed on the hardness of the leading member in the present invention, because the trailing member can exhibit its effects insofar as its hardness measured by a similar method is higher than the hardness of the trailing member. For enabling to maintain firm connection with a plunger rod formed of a general plastic material, however, it is preferred to construct such that the trailing member is provided with a hardness of at least 75 or so in terms of the Shore A hardness. The connection with the plunger rod becomes more firm with the hardness of the trailing member. It is, however, meaningless to make the hardness of the trailing member higher than the hardness of the plunger rod. When the leading member is constructed as described above, the leading member is provided with flexibility, is allowed to smoothly and repeatedly slide on and along the wall that defines the narrow space in the syringe barrel, and can sufficiently perform its function as a piston. On the other hand, the trailing member is integrated with the leading member, and can sufficiently perform its function as a joint for firmly connecting the plunger rod to the piston.

The leading member 1, which constitutes the one of the sections of the piston according to the present invention, can be produced with such an elastic material as mentioned above by a conventional molding method. Preferably, however, the leading member 1 of the piston may be laminated (covered) with a plastic film to provide it with improved slidability or to protect a drug solution, which is to be filled in a syringe barrel, from contamination with one or more raw material components that form the piston. Described specifically, the leading member 1 may be covered preferably with a resin selected from fluorinated resins, polyethylene resin, polypropylene resin and ultra high molecular polyethylene resin. For example, the leading member 1 may preferably be produced in a form that the leading member 1 is laminated (covered), over at least a surface thereof where it comes into contact with the drug solution, with a plastic film of a fluorinated resin or the like having a thickness of from 30 to 100 μm or so. In this case, it is preferred to keep at least a bottom wall portion of the leading member 1, or as depicted in FIG. 5(*a*) and FIG. 5(*b*), the bottom wall portion and its adjacent area 1' of the leading member 1 unlaminated with the plastic film so that the welding of the leading member 1 and trailing member 2 can be facilitated. Further, the lamination of a material, which has high weldability with both the members, on the bottom wall portion is effective as a method for facilitating the welding of the leading member 1 and trailing member 2.

One example of the leading member 1 constituting the one of the sections of the piston according to the present invention is shown in FIG. 2. By dividing the leading member 1 into a top section 1A and a bottom section 1B, their shapes and structures will be described hereinafter. Firstly, the leading member 1 is required to be smoothly slidable while exhibiting good sealing performance without leakage in a state that the syringe barrel is filled with the drug solution and the leading member 1 is maintained in contact with the drug solution. The top section 1A that makes up the upper section of the leading member 1, therefore, has a top wall 3 capable of dividing the cylindrical space of the syringe barrel such that the filled drug solution can be retained in the space and the leading member 1 can smoothly slide in the narrow space. To enable the leading member 1 to smoothly slide on and along the wall that defines the space in the syringe barrel, it is preferred that the top wall 3 is formed of a gently-curved wall having an apex and that a shoulder portion 4 as a boundary area between the top wall 3 and a side wall 5 is not angular but has a curved smooth surface. To achieve both sealing performance and slidability, the top section 1A may preferably be formed in such a shape as will be described below. Firstly, at least one groove is formed at the shoulder portion 4. In the example shown in FIG. 2, two shallow grooves are formed, and moreover, a relatively deep groove is also formed at the boundary between the shoulder portion 4 and the side wall 5. Further, the side wall 5 which extends from the shoulder portion 4 may preferably be formed, as shown in FIG. 2, of a curved wall bulging at a middle part thereof. By constructing the top section of the leading member 1 as described above, the piston according to the present invention has a structure that its side wall can be maintained in close contact with the inner wall of the syringe barrel without any gap therebetween and sealing performance and slidability can be both satisfied.

No particular limitation is imposed on the bottom section 1B which makes up the lower section of the leading member 1 and extends from the above-described top section 1A, insofar as the bottom section 1B has a structure that enables welding with the trailing member 2 to be described subsequently herein. With the top section 1A of such a shape as mentioned above, the piston can satisfy both sealing performance and slidability. More preferably, the bottom section 1B may be constructed in such a shape as will be described below. Firstly, a gently-constricted portion is formed between the top section 1A and the bottom section 1B, and further, the bottom section 1B is formed at a side wall 6 thereof in the shape of a curved wall bulging at a middle part thereof like the top section 1A. In addition, the bottom section 1B is formed such that, as shown in FIG. 2, it is gradually reduced in diameter toward the bottom wall to form a taper. Moreover, the leading member 1 may preferably have substantially the same outer diameter as the trailing member 2 at welded parts thereof when the leading member 1 has been welded with the trailing member 2 as a connecting member to a plunger rod 20. To provide the welded portions with high joint strength when the bottom section 1B is welded with the trailing member 2, it is also preferred to form a recess 7 through the bottom wall of the bottom section 1B to fit a protrusion 2A, which is arranged at the forward end of the trailing member 2, in the recess 7, and then to weld the bottom section 1B and the trailing member 2 in the fitted state. No particular limitation is imposed on the shape of the recess 7, insofar as it can be fitted on the protrusion 2A arranged at the forward end of the trailing member 2 to be described subsequently herein and subsequent welding can firmly connect the leading member 1 and trailing member 2 together. It is to be noted that the recess 7 may be omitted if sufficient joint strength can be obtained.

Figure 3:
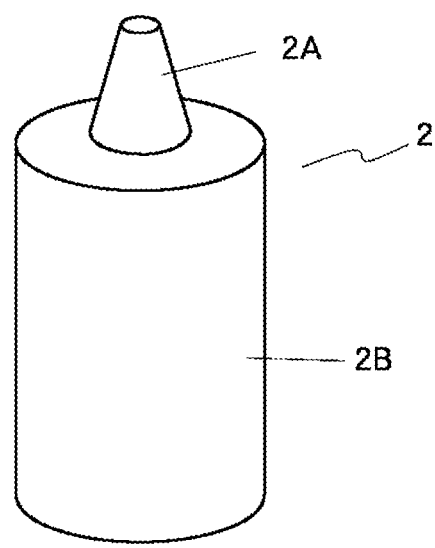
FIG. 3 is a perspective view of a trailing member constituting another section of the piston of FIG. 1.

In FIG. 3, one example of the shape of the trailing member 2 constituting the other section of the piston according to the present invention is depicted. The present invention is, however, not limited to this example. For example, trailing members of such shapes as depicted in FIG. 6(*a*) to FIG. 6(*c*) can also be used. About the trailing member 2, a description will hereinafter be made by dividing it into the protrusion 2A arranged at a forward end thereof and the main body 2B. As the shape of the protrusion 2A, one having a flat wall at least at a forward end portion thereof is preferred to permit integrating the main body 2B with the bottom wall of the bottom section 1B, which constitutes the other section of the leading member 1, in a good state. These leading member and trailing member are integrated together by a method such as, for example, welding. In such a case, the leading member and trailing member may be constructed preferably in such structures that to prevent the resins from flowing out, the outer diameter of the flat wall of the trailing member before the integration is smaller than the outer diameter of the bottom wall portion of the leading member before the integration. It is also preferred to form a recess through the bottom wall of the bottom section 1B constituting the other section of the leading member 1 and to provide the forward end portion of the trailing member 2 with a protrusion of a shape that the protrusion can be fitted in the recess.

As the shape of the trailing member 2, especially as the shape of the protrusion 2A arranged at the forward end portion of the trailing member 2, those depicted in FIG. 6(*a*) to FIG. 6(*c*) can be mentioned by way of example. For example, it is preferred to form the trailing member 2 in such a shape as depicted in FIG. 6(*b*) or FIG. 6(*c*) and to integrate the leading member 1 and trailing member 2 together by conducting welding as depicted in FIG. 5(*b*), because the fused resins can be prevented from flowing to an outside beyond an outer circumference of the trailing member 2. It is to be noted that the trailing members of FIG. 6(b) and FIG. 6(c) are not provided with a portion capable of fitting in a recess which can be formed through the bottom wall of the bottom section 1B constituting the other section of the leading member 1 and which has such a shape as shown in FIG. 2. If they are further provided with a portion (not shown) capable of fitting in the recess, more firm connection is feasible when integrated. Further, the bottom wall of the main body 2B of the trailing member 2 needs to be provided with a structure for enabling the connection of a plunger rod by a method such as threaded engagement. This structure can be any suitable structure such as a female thread or a ridge. Preferably, however, the main body 2B may be formed in a cylindrical shape provided in a bottom wall thereof with a bore, and the bore may be provided on an inner wall thereof with a ridge 8 threadedly engageable with a male thread arranged on a tip of the plunger rod.

As the material for forming the trailing member 2, a material similar to such a forming material as mentioned above in connection with the leading member 1 can be used, although the material for forming the trailing member 2 is required to have a higher hardness than the material for forming the leading member 1. Especially when a completely cross linked, thermoplastic elastomer which enables thermal welding with another resin is used as the forming material for the leading member 1, the use of a similar thermoplastic elastomer as the forming material for the trailing member 2 is a preferred embodiment from the standpoint of the strength of the joint with the leading member 1. Of course, other general-purpose resins such as PP (polypropylene), PE (polyethylene), ABS resin, PC (polycarbonates), PA (polyamides) and PMMA (polymethyl methacrylate) can also be used. Among these, the use of PE, PP, PC or the like is preferred for its low cost and excellent strength and hardness.

Figure 4:
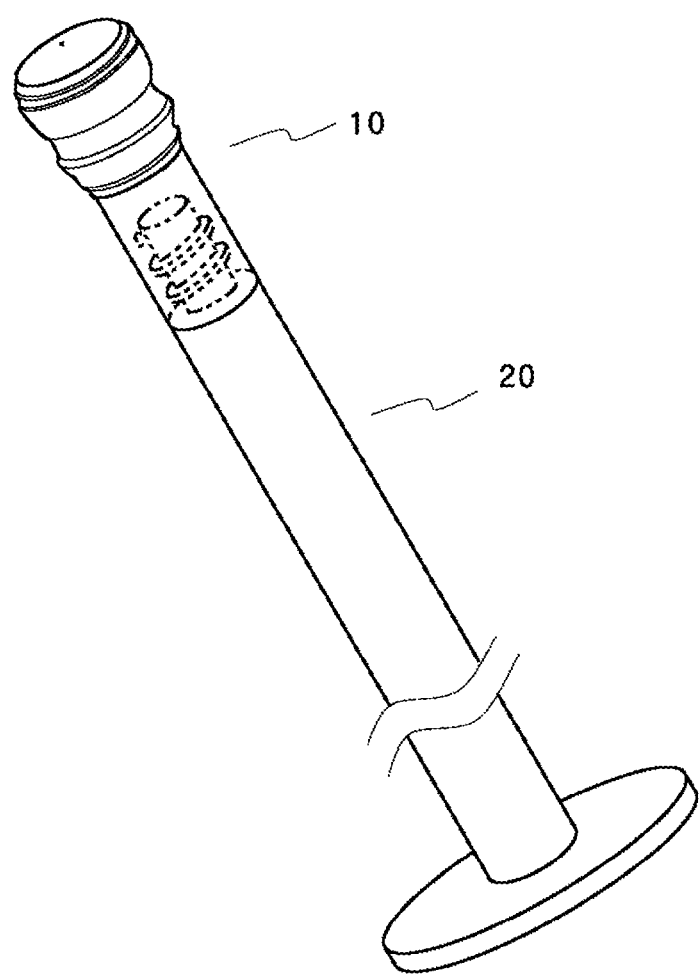
FIG. 4 is a perspective view for describing a plunger with the piston of FIG. 1 connected to a tip of a rod.

In FIG. 4, a plunger comprised of the piston 10 according to the present invention and the plunger rod 20 connected thereto is illustrated as a perspective view. The plunger 10 is illustrated on an enlarged scale in the figure than the actual product. Assuming, for example, that the piston 10 according to the present invention is for a 0.25-mL syringe, its size can be as follows: the leading member 1—approx. 4.0 mm diameter× approx. 4.5 mm height, or so; the trailing member 2—approx. 3.0 mm diameter× approx. 7.0 mm height, or so. The integration of the leading member 1 and trailing member 2 can be conducted by a method such as heating portions of the respective members, said portions being to be welded together, beforehand, fitting both the members together while they are heated, and then annealing them while holding them in a closely-contacted state.

EXAMPLE

The present invention will hereinafter be described in further detail based on an example.

Using chlorinated butyl rubber ("HT1066", product of Exxon Mobil Corporation) as a synthetic rubber, a leading member 1 was produced as many as 20 pieces. Each leading member 1 was laminated at a solution-contacting-side surface thereof with PTFE ("TEFLON® 7A", product of E.I. du Pont de Nemours and Company) as a film of approx. 100 μm thickness, and had a size of approx. 4.0 mm diameter× approx. 4.5 mm height and the shape shown in FIG. 2. The leading member 1 was measured for hardness, and as a result, its hardness was found to be 50. Using SEBS ("ELASTOMER AR800", product of Aron Kasei Co., Ltd.) as a forming material, on the other hand, a trailing member 2 having a size of approx. 3.0 mm diameter×approx. 7.0 mm height and the shape shown in FIG. 3 was produced as many as 20 pieces. The trailing member 2 was measured for hardness, and as a result, its hardness was found to be 75. The protrusion at a forward end of each trailing member 2 and the recess arranged on the side of the bottom wall of its corresponding leading member 1 were heated to a temperature of from 140 to 160° C. or so such that the heated portions became soft. Immediately after the heating, the protrusion at the forward end of the trailing member 2 was fitted in the recess of the leading member 1, followed by annealing while holding them in the fitted state.

As a result, twenty (20) pistons of the invention example were obtained. In the bores of the trailing members 2 constituting the other sections of the respective pistons, plunger rods of approx. 3 mm diameter×approx. 55 mm length were then inserted and fixedly fitted to obtain plunger rods with the pistons connected to tips of the plunger rods. Using those plunger rods separately, the pistons were each caused to slide back and forth 10 times in a 0.25 mL syringe barrel. As a result, the piston connected to the front tip did not fall off from the plunger rod in each piston-connected plunger rod. Of course, it was possible to smoothly perform the drawing and ejection of a solution without leakage.

In a similar manner as described above except that the forming material for the trailing member 2 of the shape depicted in FIG. 3 was changed to polypropylene ("HI-ZEX", product of Mitsui Chemicals, Inc.), plunger rods with pistons connected to tips thereof were obtained. With respect to those plunger rods with the pistons connected to the tips thereof, a similar test was conducted. As a result, the piston connected to the tip did not fall off from the plunger rod in each piston-connected plunger rod. Of course, it was possible to smoothly perform the drawing and ejection of the solution without leakage.

LEGEND

1 Leading member
2 Trailing member
3 Top wall
4 Shoulder portion
5 Side wall
6 Side wall
7 Recess
8 Ridge
10 Piston
20 Plunger rod

The invention claimed is:
1. A piston for a micro-volume syringe having a syringe barrel with a space defined therein, said piston comprising a leading member and a trailing member and being slidable on and along a wall of the space, wherein
 the leading member is arranged on a first side of the piston where the piston comes into contact with a solution filled in the space, the leading member includes a side wall and a top wall that forms an entire top surface of the leading member facing the solution filled in the space, and the top wall has no openings therein,
 the trailing member is arranged on a second side of the piston where a plunger rod is to be connected, the second side being opposite to a solution side of the leading member,
 the leading member comprises a first recess formed on a bottom surface of the leading member located on the second side,
 the trailing member comprises a main body having a forward end surface located on a first side facing the leading member, a bottom end surface located on a second side opposite the first side of the trailing member, and an exterior side wall extending between the forward end surface and the bottom end surface, the main body having an outermost diameter, a second recess formed on the bottom end surface to which the plunger rod is to be connected, a terminal end of the second recess is formed by an innermost surface, and the innermost surface is between the bottom end surface and the forward end surface, a protrusion protruding directly from the forward end surface, the protrusion having a diameter that is less than the outermost diameter of the main body, and the outermost diameter of the main body is constant from the bottom end surface to a position that is level with the terminal end of the second recess formed by the innermost surface, the leading member has an outermost diameter that is greater than the outermost diameter of the main body, the protrusion is welded with the first recess in a state in which the protrusion is fitted in the first recess, a distance from the innermost surface of the second recess to the bottom end surface being smaller than a distance from the forward end surface to the bottom end surface, and the trailing member has a higher hardness than the leading member.

2. The piston according to claim 1, wherein the leading member is formed of a material, which is composed as a primary component of a material selected from the group consisting of synthetic rubbers and thermoplastic elastomers and which has a Shore A hardness of from 40 to 70.

3. The piston according to claim 1, wherein the trailing member is formed of a material, which is selected from the group consisting of polyethylene, polypropylene, polycarbonates and thermoplastic elastomers and which has a Shore A hardness of 75 or higher.

4. The piston according to claim 1, wherein the top wall of the leading member is covered with a resin selected from the group consisting of fluorinated resins, polyethylene resin, polypropylene resin and ultra high molecular polyethylene resin.

5. A piston-connected plunger wherein the plunger rod is threadedly connected at a tip thereof to a ridge arranged on an inner wall of the second recess of the trailing member of the piston according to claim 1.

6. The piston according to claim 1, wherein the leading member and the trailing member are welded at abutting flat surfaces.

7. The piston according to claim 6, wherein the abutting flat surfaces extend substantially perpendicular to a longitudinal axis of the piston.

8. A micro-volume syringe comprising the piston according to claim 1 and the syringe barrel.

9. The piston according to claim 1, wherein the outermost diameter of the main body is substantially constant from the bottom end surface to the forward end surface thereof.

* * * * *